United States Patent [19]

Pridemore

[11] 4,216,777
[45] Aug. 12, 1980

[54] METHOD FOR ARTIFICIALLY IMPLANTING HAIR

[76] Inventor: William J. Pridemore, P.O. Box 883, Clemson, S.C. 29631

[21] Appl. No.: 812,347

[22] Filed: Jul. 1, 1977

[51] Int. Cl.³ ............................................. A61B 17/00
[52] U.S. Cl. .................................................. 128/330
[58] Field of Search ................... 128/330, 329 R, 1 R; 3/1

[56] References Cited

U.S. PATENT DOCUMENTS

| | | | |
|---|---|---|---|
| 1,059,631 | 4/1913 | Popovics | 128/330 |
| 3,003,155 | 10/1961 | Mielzynski et al. | 128/330 X |
| 3,699,969 | 10/1972 | Allen | 128/330 |
| 3,998,230 | 12/1976 | Miller | 128/330 |
| 4,004,592 | 1/1977 | Yamada | 128/330 |
| 4,126,124 | 11/1978 | Miller | 128/1 R |

FOREIGN PATENT DOCUMENTS 1953026  2/1972  Fed. Rep. of Germany ........... 128/330

Primary Examiner—Robert W. Michell
Assistant Examiner—Michael H. Thaler
Attorney, Agent, or Firm—Bailey, Dority & Flint

[57] ABSTRACT

A method and apparatus for artificially implanting hair in human skin tissue is disclosed wherein a strand of hair is folded upon itself to define a pair of strands joined together by a U-shaped bend at which an enlarged anchor element is provided to be implanted in the skin with the strand of hair exposed above the surface. The apparatus includes a plurality of needles carried in a side-by-side relationship on a base member each needle having an interior bore in which the anchor element is held with the hair strands held by a hair clamp on the enterior of the needle. The needle is inserted into the skin and the anchor is dislodged therefrom whereupon withdrawal of the needle leaves the anchor implanted with the hair strands exposed above the skin surface.

4 Claims, 29 Drawing Figures

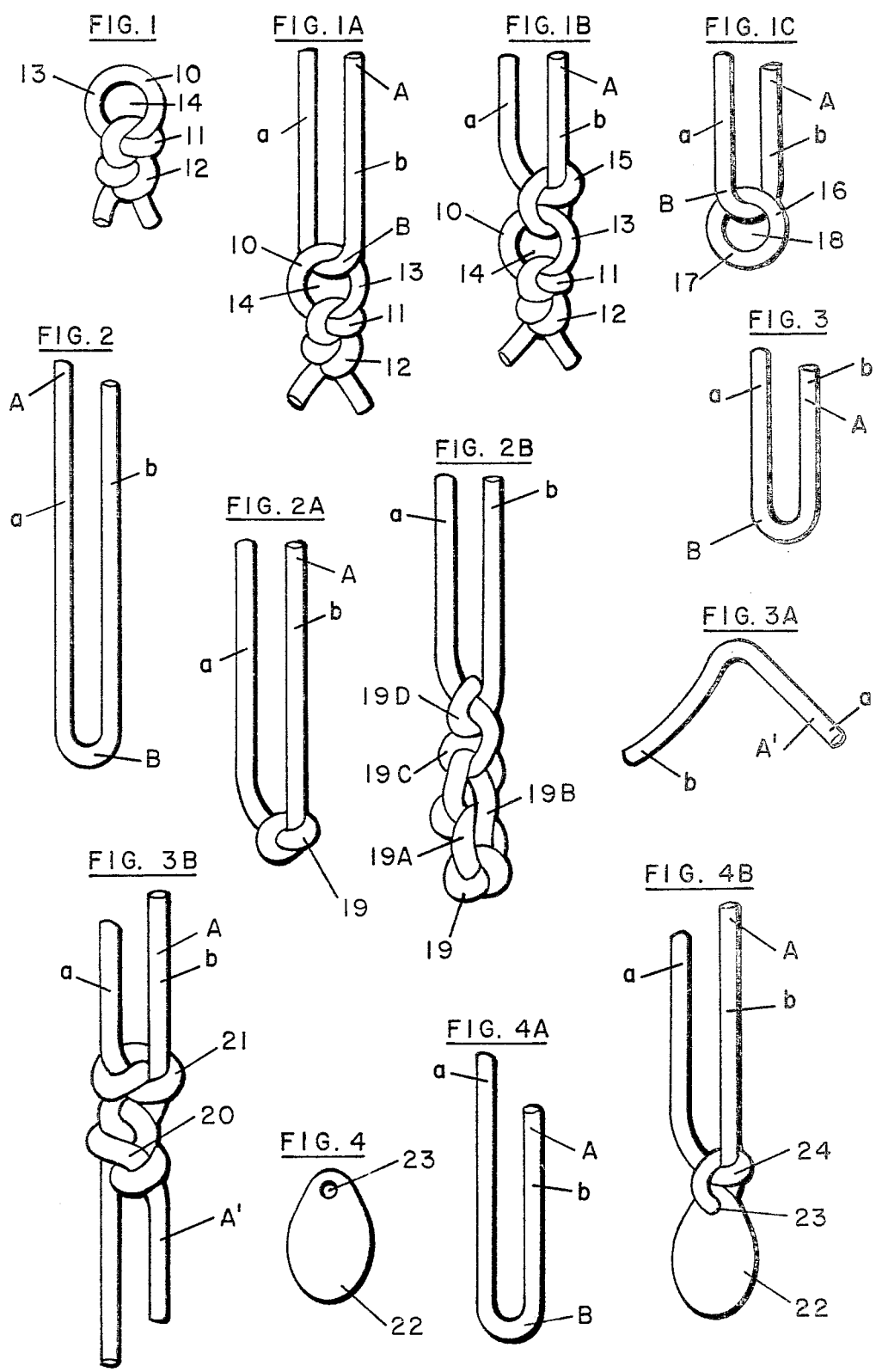

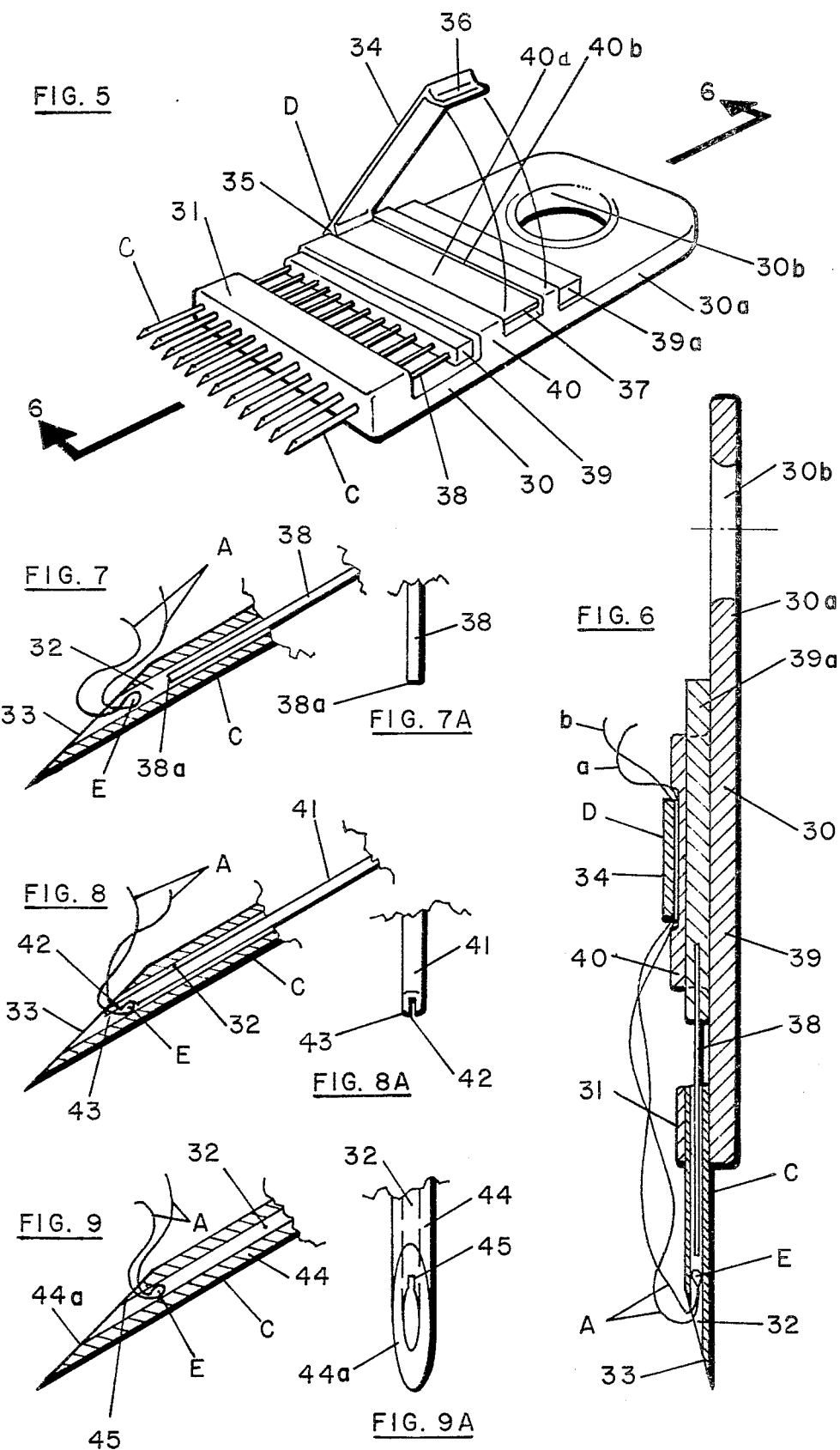

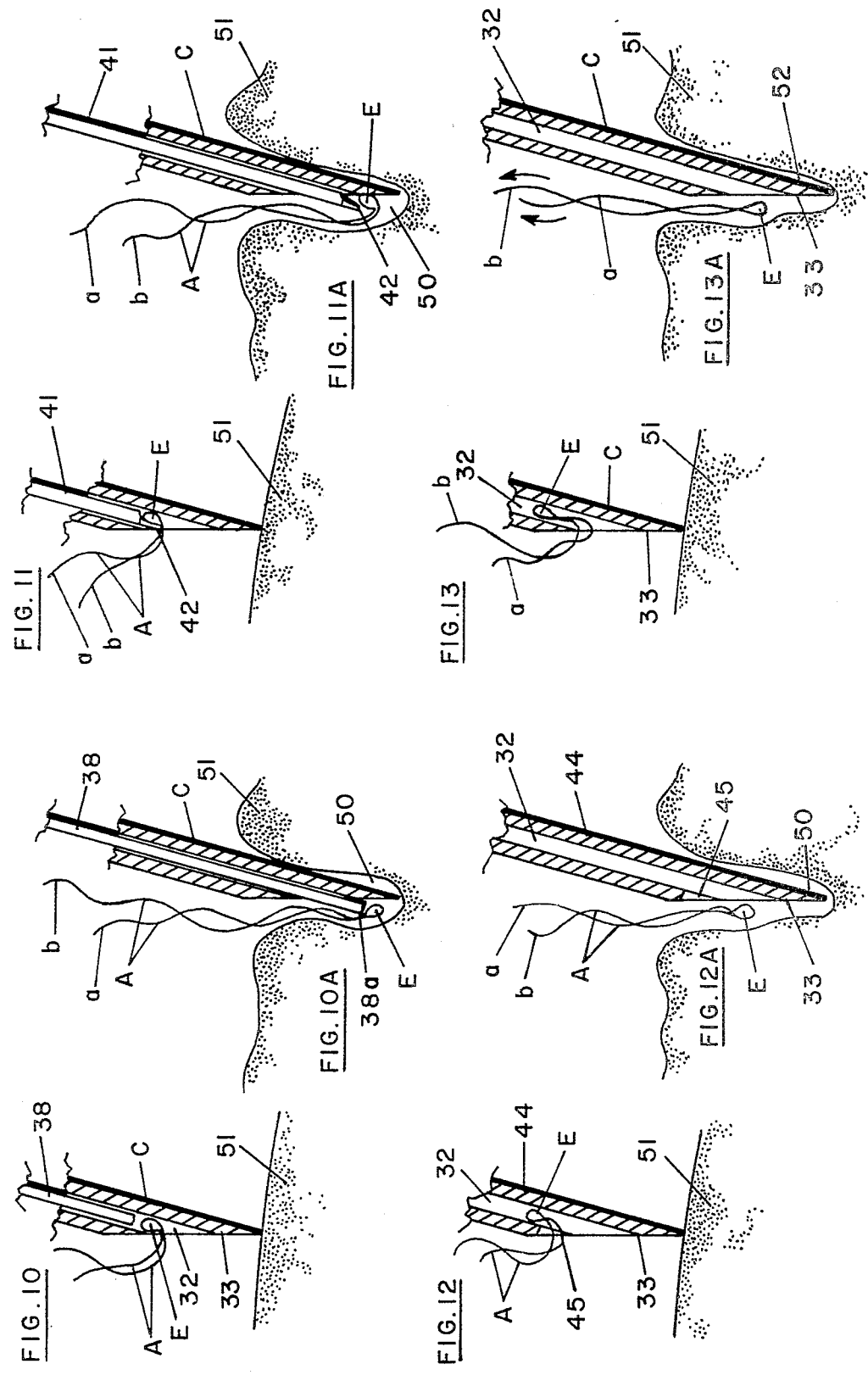

METHOD FOR ARTIFICIALLY IMPLANTING HAIR

BACKGROUND OF THE INVENTION

Hair implants have become increasingly popular for providing an artificial hair covering over bald areas of a human scalp. However, the success of prior artificial hair implants has been limited mainly due to the unnatural cosmetic appearance of the implanted hairs and the loss of implanted hairs during combing and brushing resulting from inadequate anchoring. Various methods have been heretofore proposed for anchoring the implanted hairs into the scalp such as by forming a plurality of knots at the end of a strand of hair as shown in U.S. Pat. No. 3,998,230. However, the knotting of a single strand of hair is a tedious and time consuming operation and knotting strictly at the end of a single hair often results in the knot slipping off the end of the hair when tugged excessively during brushing and combing.

U.S. Pat. No. 3,699,969 discloses a method for implanting a natural or synthetic hair utilizing a disk-shaped member having a number of perforations through which the ends of the artificial strands are inserted and then knotted. U.S. Pat. No. 4,004,592 discloses another method for implanting and anchoring an artificial hair in human skin tissue which utilizes a one-piece artificial hair strand having an enlarged root portion made as one piece with the trunk portion of the strand which extends above the stem surface. A problem encountered during the implant process with the prior apparatus is that the hair strand is normally carried within the bore of the needle with the anchor portion carried either within the bore or exterior of the needle. The problem occurs in that skin tissue is often lodged around the open end of the needle during insertion into the skin tissue causing the hair to bind in the opening and pull out when the needle is withdrawn from the scalp instead of sliding relative to the needle. While U.S. Pat. No. 3,699,969 utilizes a plurality of strands anchored by a single anchor member, the strands are knotted at the ends which increases the tendency of the knots to slip off of the end of the hair when tugged upon sufficiently during brushing.

Accordingly, an important object of the present invention is to provide a method and apparatus for implanting a natural or artificial hair fiber wherein the implanted hair is anchored securely and has a natural appearance.

Another important object of the present invention is to provide a method and apparatus for implanting a plurality of hair strands at a time.

Another important object of the present invention is to provide a method for artificially implanting a hair strand wherein the strand is anchored by a knotting arrangement which cannot slip off of hair strands during tugging.

Still another important object of the present invention is to provide an improved method for artificially implanting a strand of hair wherein the hair strand is carried about the exterior of the implant needle avoiding binding of the hair strand inside the needle due to lodging of skin tissue during needle insertion.

SUMMARY OF THE INVENTION

It has been found that a method and apparatus for artificially implanting a strand of hair into human skin tissue may be provided by an implanting tool having at least one implant needle with an interior bore and a clamp for holding the hair exteriorly of the needle and by a single strand of hair folded to provide a pair of strands joined by a U-shaped bend portion with an improved anchor element secured at the bend portion. The method contemplates placing the anchor element in the front end of the needle bore with the hair strand held about the exterior of the needle and inserting the needle in the skin tissue and dislodging the anchor element from the interior of the needle as the needle is withdrawn with the hair strand on the exterior thereof. In this manner, binding of the strand within the needle bore is avoided as the needle is withdrawn from the skin tissue leaving the anchor element embedded in the tissue with the hair strand being exposed above the skin surface. In the preferred embodiment, the improved anchor is provided by an annular element having a narrow outer rim and an enlarged medial opening pervious to the growth of skin whereby the anchor is secured by knotting the strand over the outer rim at the bend portion.

BRIEF DESCRIPTION OF THE DRAWINGS

The construction designed to carry out the invention will be hereinafter described, together with other features thereof.

The invention will be more readily understood from a reading of the following specification and by reference to the accompanying drawings forming a part thereof, wherein an example of the invention is shown and wherein:

FIGS. 1 through 1C illustrate a preferred embodiment of a method for forming an anchor element on a hair strand in accordance with the present invention, FIGS. 2 through 2B illustrate an alternate embodiment of the method for implanting and anchoring an artificial hair strand, FIGS. 3 through 3B illustrate another embodiment of a method for anchoring an artificial hair strand in accordance with the present invention, FIGS. 4 through 4B illustrate another embodiment of a method for anchoring an artificial hair strand in accordance with the present invention, FIG. 5 is a perspective view illustrating apparatus for implanting an artificial hair strand in accordance with the present invention, FIG. 6 is a sectional view taken along line 6—6 of FIG. 5, FIG. 7 is a cut-away view illustrating an implant needle and plunger apparatus constructed in accordance with the present invention, FIG. 8 is a cut-away partial section view illustrating an implant needle and alternate plunger apparatus constructed in accordance with the present invention, FIG. 9 is a cut-away partial section view illustrating an alternate embodiment of an implant needle constructed in accordance with the present invention, FIGS. 10 through 10A are schematic views illustrating a method for artificially implanting a hair strand in accordance with the present invention, FIGS. 11 and 11A are schematic views illustrating a method for artificially implanting a hair strand in accordance with the present invention utilizing the apparatus of FIGS. 8 and 8A, FIGS. 12 and 12A are schematic views illustrating a method of artificially implanting a hair strand in accordance with the apparatus of FIGS. 9 and 9A, and FIGS. 13 and 13A are schematic views illustrating another method and apparatus for artificially implanting a hair strand in accordance with the present invention.

DESCRIPTION OF A PREFERRED EMBODIMENT

The drawings illustrate a method and apparatus for implanting a synthetic or natural strand of hair into the skin tissue of a human scalp. The method contemplates providing a single strand of hair A and folding the strand upon itself to form a pair of strands a and b joined together by a U-shaped bend portion B. Various forms of anchor elements are provided which are secured at the bend portion whereby implantation of the anchor can be had with the pair of strands exposed above the skin surface. The bend portion is preferably formed midway between the two ends of the strand A and, in actuality, the anchor element is, in most instances, secured prior to folding the strand such as by knotting. Of course securing the anchor and folding the strand at some other point intermediate the ends thereof may be done, however, it is normally desired that the two resulting strands a and b be of approximate equal length which can be accomplished by trimming.

The implanting apparatus of the present invention includes at least one implant needle C having a hollow bore and an open pointed end for holding the anchor element during insertion into the scalp with the pair of strands extending from the open end held on the exterior of the needle by a hair clamp D. Various embodiments of the invention are disclosed for dislodging the anchor element from inside the front end of the needle and implanting same into the scalp.

Referring now in detail to FIGS. 1–1C, a preferred embodiment is illustrated wherein an anchor element 10 is provided by a strand of hair tied in one or more knots 11 and 12 to define an annular element having a narrow outer rim 13 and an enlarged medial opening 14 pervious to the growth of skin. The strand A is threaded through opening 14 and then, preferably at the middle of the bend B, knotted over the rim 13 in one or more tight knots 15. In the alternative, the anchor element is provided by a continuous ring 16 of synthetic material such as nylon rather than the knotted ring 10. The ring 16 likewise has a narrow rim 17 about which strand A is knotted similarly as described above and a medial opening 18.

The embodiment of FIGS. 2–2B utilizes the strand A, itself, in forming the anchor element by knotting the strand upon itself at 19 in the area of bend B. Additional knots 19a–19d may be formed as necessary to enlarge the anchor portion 19.

FIGS. 3–3B contemplate the use of two like strands A with one strand A' knotted or woven over the strand A in the middle or bend portion B at 20. Strand A is then knotted at 21 over the knot 20 in strand A' to prevent strand A from being pulled through the knot of anchor strand A'. Strand A' may also be woven about strand A rather than conventional knotting.

In the embodiment of FIG. 4, the anchor portion is provided by a solid element 22 of any suitable synthetic material having a size approximate to that of the knotted and ring anchors heretofore described and a substantially pear-shape. The strand A is threaded through an opening 23 and then knotted at least once at 24 in the bend portion about the element 22.

It will be noted that in all of the embodiments heretofore described, the anchor element or portion is secured about the middle bend portion B with the strands a and b protruding above the scalp after implant. In all instances, the strand A and associated anchor element are mutually secured so that it is virtually impossible for either strand a or b to be pulled through and free from the anchor during hard pulling such as from brushing or combing. The embodiment of FIG. 1 is particularly advantageous in that it anchors the strand not only by being enlarged or bulbous as a root, but also because the opening 14 or 18 is enlarged sufficiently to allow skin to grow therethrough solidifying its anchor effect.

There may be some applications where only a single strand exposed above the scalp is desired, such as implants on the front hair line in order to simulate a more natural appearance. In this case, either strand a or b may be trimmed so as not to be exposed after implant without impairing the anchor portion.

The apparatus of the present invention, as illustrated in FIG. 5, includes a base member 30 having a block portion 31. A plurality of the hypodermic type needles C are carried by the block member 31 with each needle having a longitudinal interior bore 32 and an open pointed end 33 through which the anchor element shown schematically as E is received for placement in the bore. The element E, of course, may be any of the anchors described in relation to FIGS. 1–4 above. The clamp means D is carried by the base member and in the preferred form includes a clamp bar 34 hinged at 35 to the base 30 and having a clamp lip 36 which cooperates with an integral base lip portion 37 for locking engagement therewith. The base 30 includes a handle portion 30a for convenience with a gripping opening 30b formed therein.

A plurality of push rods 38 are carried by a block 39 which slides on base 30 within a hollow bridge frame 40 integral or formed as one-piece with the base which also incorporates clamp means D therein. The push rods 38 enter the rear of interior bore 32 through an open end 33a of the needle remote from the pointed end 33 for dislodging the anchor E. It will be noted that a push rod is provided for each needle in alignment with the bore thereof. The block may be pushed forward at a rear portion 39a to dislodge a plurality of anchors E simultaneously into skin pits formed by insertion of the needle point.

In the embodiment of FIG. 7, the push rod or plunger 38 is shown having a flat end 38a. However, other advantageous forms may be had for the plunger such as providing a plunger 41 having a narrow open ended slit 42 in a contoured or tapered end 43 whereby the anchor is held under the contoured portion with the strand A extending through the slit during insertion. In FIG. 9, an implant needle 44 is shown which does not utilize a plunger to remove the anchor element E. Instead, an open ended slit 45 is provided on a beveled edge 44a of the needle itself for holding the strand and anchor in the same manner as slit 42 of plunger 41. The anchor E is removed by withdrawing the needle with the strand A on the exterior thereof.

Referring now to FIGS. 10–13, several embodiments of implant apparatus and methods are discussed. FIG. 10 illustrates implanting the anchor portion E with the needle C and plunger 38 of FIG. 7. It will be noted that in all of the above figures, the strand A is held on the exterior of the needle C with the anchor E received in the hollow bore 32 of the needle. The strand pair a and b created by knotting strand A are held by the clamp D as being clamped between clamp bar 34 and the clamping surface 40a and edge surfaces 40b of bridge 40. As illustrated in FIG. 6, the strands a and b extending from each needle C are clamped whereby a plurality of strands are conveniently and necessarily held exteriorally during insertion of the needle to create a skin pit 50 in the skin tissue 51 for implant of the hair. Such clamping maintains adequate tension on strands a and b to prevent anchor E from accidental dislodge during insertion and, of course, prevents the strands from becoming entangled and from interferring with the insertion of the needle.

Implant with the apparatus and methods of FIGS. 10-13 will now be discussed with reference to a single needle with it being understood that the same applies to implant with a plurality of needles utilizing the multi-needle device of FIG. 5. Following insertion of the needle C, the strands a and b are released from the clamp means D. In FIG. 10, the push rod 38 is then pushed forward whereby the flat end portion 38a dislodges the anchor E into the skin pit formed by the needle. The needle is withdrawn from the skin with the push rod in its forwardmost position, such as shown in FIG. 10A, depositing the anchor portion E in the skin pit wherein the strands and anchor are implanted after the needle is completely withdrawn.

A second embodiment is illustrated in FIG. 11 wherein the needle and push rod of FIG. 8 are utilized in the implant procedure. The hair strands a and b are received within the narrow slit 42 with the anchor portion E held beneath the contoured portion 43. When the push rod 41 is pushed to its forward position and extracted with the needle, the hair strands slide out between the slit as best illustrated in FIG. 11A. Of course, prior to extraction, the strands a and b are released from the clamp D leaving them protruding from the scalp tissue 51 following implant. It will be noted that the anchor E is positively pushed out of the needle C by the push rod and that the entire strand A including the anchor E is outside of the needle bore 32 immediately preceding withdrawal of the needle avoiding any tendency of the hair strand to pull out with the needle.

FIG. 12 illustrates the implant needle of FIG. 9 wherein the strand A is received in the slit 45 which is formed in the needle point itself eliminating the use of a push rod as heretofore described. In this embodiment, the anchor E is also held below the slit opening 45 by the opposing forks on each side of the slit. After the anchor portion is so inserted in the front of the needle, the two strands a and b are held on the exterior of the needle such as by clamp means D, although in the case of a single needle manual holding may also be utilized. After the needle is inserted into the scalp 51, the strands are released from whatever means they are held and the needle is extracted from the scalp forcing the hair strands to slide from the slit leaving the anchor embedded in the skin pit with the strands exposed above the skin surface. It will be noted that in all of the methods thus described the hair strand or strands are gripped between the skin and needle surfaces so that as the needle is withdrawn the hair does not slide out with the needle but due to friction with the skin remains in position. The hair and anchor portions are accordingly forced from their held position in the front of the needle during withdrawal and implanted. For this reason, the needle exterior must be kept smooth so as to slide relative to the skin and hair at all times and not to damage the hair.

As illustrated in FIG. 13, a plain needle C is utilized in the implant method for the present invention without a push rod or a slit as previously described. In this case, the anchor portion E is merely placed in the front of the open ended needle and the hair strands a and b are held on the exterior of the needle. The needle is inserted slightly deeper than is necessary with the other described methods and apparatus to form a slightly deeper skin pit 52. After insertion the strands are released and pulled backwards until the anchor E slides out of the end of the needle 33 and into place in the pit 52. The needle is then extracted leaving the anchor implanted with the strands protruding above the scalp.

Thus, it can be seen that an advantageous construction for an apparatus and method can be had in accordance with the present invention for artificially implanting hair. The arrangement whereby a single strand is knotted with an anchor portion provides two hairs protruding from the same skin pit for twice as much coverage affording savings in time and costs while enhancing the cosmetic appearance. The hair is made thicker since hairs can be implanted more closely together resulting a a more natural hair line.

Implant with the hair strands held on the exterior of the implant needle avoids the pulling out of hair during needle extraction which often occurs in prior methods where the entire length of the hair is held within the needle and must slide out of the open end of the needle. Due to clogging of skin tissue in the needle opening, the hair often becomes bound and cannot slide relative thereto resulting in pulling out of the hair with the needle. In accordance with the present invention only the anchor portion is held within the needle which is easily and reliably removed with a push rod or other method disclosed. Knotting the hair strand and the anchor element in the U-shaped bend portion of the hair with the two hair ends extending up from the bend prevents the knot and anchor from slipping off of the end of the hair as might be the case where knots are formed strictly on the end of a single hair. This effectively reduces the likelihood that the hair will pull or slip from the anchor when tugged upon during brushing and combing prolonging the life of the implant.

While a preferred embodiment of the invention has been described using specific terms, such description is for illustrative purposes only, and it is to be understood that changes and variations may be made without departing from the spirit or scope of the following claims.

What is claimed is:

1. A method of artificially implanting a hair in the human skin tissue comprising the steps of:
   providing a single strand of hair;
   providing an enlarged anchor which includes a second strand having an annular configuration;
   securing said anchor to said single strand intermediate the ends thereof by knotting said strand about said anchor;
   folding said single strand upon itself about said anchor strand to define a pair of strands extending from said anchor so that said anchor is secured between said pair of strands within a bend portion thereof; and
   implanting said anchor in said skin tissue with said pair of strands exposed above the skin surface.

2. The method of claim 1 wherein said enlarged anchor is provided by a continuous annular strand element having a narrow outer rim and an enlarged medial opening pervious to the growth of skin tissue and wherein said anchor is secured by threading said strand through said medial opening and tying at least one knot in said strand over said outer rim.

3. The method of claim 1 comprising the steps of:
arranging said second strand in an open loop configuration having an outer rim and an enlarged medial opening pervious to the growth of skin tissue;

fixing said open loop configuration by knotting said second strand adjacent the ends thereof; and securing said anchor by threading said first strand through said medial opening and knotting said strand over said outer rim.

4. The method of claim 1 wherein said anchor is povided by:
weaving and knotting said second strand about said first strand.

* * * * *